United States Patent
Jagannatha et al.

(10) Patent No.: US 11,532,391 B2
(45) Date of Patent: Dec. 20, 2022

(54) SYSTEM AND A METHOD FOR IMPROVING RELIABILITY OF MEDICAL IMAGING DEVICES

(71) Applicant: KONINKLIJKE PHILIPS N.V., Eindhoven (NL)

(72) Inventors: Vijayananda Jagannatha, Bangalore (IN); Vinay Pandit, Gokarn (IN); Srinivas Prasad Madapusi Raghavan, Bangalore (IN); Rupesh Vakkachi Kandi, Kozhikode (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 464 days.

(21) Appl. No.: 16/652,084

(22) PCT Filed: Oct. 3, 2018

(86) PCT No.: PCT/EP2018/076904
§ 371 (c)(1),
(2) Date: Mar. 30, 2020

(87) PCT Pub. No.: WO2019/068760
PCT Pub. Date: Apr. 11, 2019

(65) Prior Publication Data
US 2020/0265944 A1 Aug. 20, 2020

Related U.S. Application Data

(60) Provisional application No. 62/673,438, filed on May 18, 2018.

(30) Foreign Application Priority Data

Oct. 5, 2017 (IN) .............................. 201741035304

(51) Int. Cl.
*G06F 9/44* (2018.01)
*G06F 9/455* (2018.01)
(Continued)

(52) U.S. Cl.
CPC ......... *G16H 30/40* (2018.01); *G06F 11/3688* (2013.01); *G06F 16/2246* (2019.01);
(Continued)

(58) Field of Classification Search
CPC .... G16H 30/40; G16H 40/40; G06F 16/2246; G06F 11/3688; G06N 3/0445; G06N 3/0454; G06N 3/08
See application file for complete search history.

(56) References Cited

U.S. PATENT DOCUMENTS 8,312,332 B2 11/2012 Gururaj
9,170,821 B1 10/2015 Palaniappan
(Continued)

OTHER PUBLICATIONS

Knorr et al., Security Testing for Android mHealth Apps, 8 pages (Year: 2015).*
(Continued)

*Primary Examiner* — Thuy Dao

(57) ABSTRACT

Systems and methods are disclosed for generating device test cases for medical imaging devices, which are not only reflective of current actual field usage of the device but also provide outlook on future usage. A probabilistic model of usage patterns is generated from historic data present in the device field logs by mining the current usage patterns. A Deep Long Short Term Memory Neural Network model of the usage patterns is constructed to predict the future usage patterns. Additionally, to capture the changing trends of device usage patterns in the field, predictive models are
(Continued)

continuously updated in real time, and the test cases generated log files by the models are integrated into an automated testing system.

27 Claims, 15 Drawing Sheets

(51) Int. Cl.
| | |
|---|---|
| H04N 7/14 | (2006.01) |
| H04N 7/15 | (2006.01) |
| G16H 30/40 | (2018.01) |
| G06F 16/22 | (2019.01) |
| G06F 11/36 | (2006.01) |
| G06N 3/04 | (2006.01) |
| G06N 3/08 | (2006.01) |
| G06N 7/00 | (2006.01) |
| G06Q 10/06 | (2012.01) |
| G16H 40/40 | (2018.01) |

(52) U.S. Cl.
CPC ......... *G06N 3/0445* (2013.01); *G06N 3/0454* (2013.01); *G06N 3/08* (2013.01); *G06N 7/005* (2013.01); *G06Q 10/0633* (2013.01); *G16H 40/40* (2018.01)

(56) References Cited

U.S. PATENT DOCUMENTS

| | | |
|---|---|---|
| 2004/0254768 A1 | 12/2004 | Yeong-Ho |
| 2007/0038039 A1 | 2/2007 | Adler |
| 2011/0113287 A1 | 5/2011 | Gururaj |
| 2011/0271219 A1 | 11/2011 | Krishnan |
| 2019/0027243 A1* | 1/2019 | Amthor .............. G06Q 10/0633 |

OTHER PUBLICATIONS

International Search Report and Written Opinion dated Feb. 18, 2019 for International Application No. PCT/EP2018/076904 Filed Oct. 3, 2018.

* cited by examiner

SYSTEM AND A METHOD FOR IMPROVING RELIABILITY OF MEDICAL IMAGING DEVICES

CROSS REFERENCE TO RELATED APPLICATIONS

This application is the U.S. National Phase application under 35 U.S.C. § 371 of International Application No. PCT/EP2018/076904 filed Oct. 3, 2018, published as WO 2019/068760 on Apr. 11, 2019, which claims the benefit of U.S. Provisional Patent Application No. 62/673,438 filed May 18, 2018 and Indian Patent Application Number 201741035304 filed Oct. 5, 2017. These applications are hereby incorporated by reference herein.

FIELD

The following relates generally to improving reliability of medical imaging devices.

BACKGROUND

Comprehensive testing of the medical devices to ensure consistent and reliable functioning is of paramount importance as hardware or software malfunctions in such devices have adverse effect on patient diagnosis process. Moreover, device failures can potentially reduce the productivity of the hospitals using them. In a conventional machine testing methodology, a field expert will prepare an operational profile, which resembles the clinical workflows that technologists perform in hospitals. An operational profile more often contains typical workflows followed for imaging of various anatomies in terms of scanning workflows and corresponding software operations. Then, the device verification team uses this profile for validating the functionalities of the machine.

There are several challenges in preparing device operation profiles comprising of comprehensive list of test scenarios. Imaging devices facilitate generating images of desired contrast by allowing the technician to modify different contrast parameters to achieve desired image contrasts. The number of such different contrast configurations used in the field is extremely high. It is required to include several such configurations in operational profiles in proportion of actual field usage.

Additionally, imaging devices enable the technologists to perform many administrative and image post-processing operations via device UI. Consequently, technologists often multi-task and work parallel on multiple patients with the help of such UI. For example, a technologist may attend to the activities like post-processing of images from the previous patient/or scan, print images, transfer images while the current scan is in progress. To ensure that medical devices perform reliably in such circumstances, it is required to include usage of all the offered UI operations in the operational profile in accordance with actual field usage.

Further, some of the advanced imaging capabilities, packaged with medical devices are compute and memory intensive, and utilizing these can potentially result in device software system hang-up or even crash. Hence, it is extremely important to include usage of those capabilities in the operation profile.

Variations in actual usage of the imaging devices in the field are another aspect, which makes envisioning comprehensive usage scenarios extremely challenging. The clinical scan sequences vary significantly based on patient's pathological conditions. For example, imaging techniques to study cellularity could be significantly different from that for analyzing brain hemorrhage. Additionally, the clinical scan sequences vary also based on hospitals' clinical practices. Moreover, hospitals continuously invent effective and improved scan sequences. Hence, there is need for extrapolating currently known scan configurations to predict future advancements and include them in the operational profile. Additionally, it is required that the operational profiles are updated continuously to capture the ongoing trends in clinical practices.

Cost and time involved in carrying out actual testing of the imaging devices impose a restriction on number of tests that can be included in an operational profile. For example, operational and maintenance cost of an MRI machine is extremely high and is estimated to be about $1000 per day. Further, average time required to complete one clinical protocol is estimated to be about 30 minutes. This implies that protocols included in the operational profiles need to succinctly represent the field usage of the imaging devices.

Imaging devices log description of all the performed scans and UI operations along with the timestamp to a log file. Further, logs contain auxiliary information to indicate start and end of clinical workflows. Event timestamps stored in log files can be used to arrange the log information into a chronological sequence of machine operations and start and end indicators can be used to extract clinical workflows. Log files, hence, are suitable for extracting insight into actual device usage in the field. Additionally, since log files can be obtained on daily basis from machine installations across the globe, they are suitable for analyzing and capturing ongoing clinical trends. Further, since log files are description of actual usage of the machine, test cases derived from log files require little validation.

The conventional testing methodology is driven by the operational profile prepared by field experts. However, those profiles are limited to experts' knowledge and often they do not adequately represent entire clinical workflows. Additionally, such profiles are rarely updated and hence may not reflect the continuously advancing clinical practices well.

In most of the busy hospitals, the technologists often multi-task and work paralleling on multiple patients or examinations. For example, a technologist may attend to the activities like post-processing of images from the previous patient/or scan, print images, transfer images while the current scan is in progress. A number of different combinations of such activities is extremely high. For example, by modifying various machine parameters a technologist can configure more than 200 unique scans. Then he/she will configure an exam by choosing a subset of such scans in a sequence that is most suitable for the current patient scenario. A typical exam will have 10 such scans, which implies that the total number of possible permutations of scans will exceed a million. Hence, it is extremely hard for an expert to identify the most probable combinations of such activities and include them in the operational profile.

Another disadvantage of the conventional testing methodologies that, often they do not include modules to predict and incorporate future usage patterns into the testing system. These methodologies are often limited to using explicitly specified test scenarios, which increases the risk of device failures when faced with unfamiliar usage patterns.

Field log files contain a wealth of information on actual usage of medical devices. However, there are a multitude of challenges in utilizing field log files to derive test usage patterns. Firstly, identifying most prominent workflows accurately is not trivial owing to variations in device usage.

For example, a technician can perform same set of scans in many different orders. Further, since several machine parameters can be modified to suit patient conditions, usage patterns are often sparsely distributed. Hence, derived test patterns may not be fully representative of the actual device usage. Additionally, it is challenging to ensure that the test patterns derived by extrapolating usage patterns found in field logs align with actual clinical usage of the machine.

In light of the above-mentioned challenges in preparing operational profile and utility of the log files, there is a need for innovative testing methodologies, which seamlessly integrate the field clinical workflows and the workflows derived by extrapolating actual workflows from field log files into a testing system.

The following discloses certain improvements.

SUMMARY

In one disclosed aspect, a system that facilitates generating a test script for a medical imaging device comprises a field log file database having stored thereon field log files comprising data related to examinations performed by one or more imaging devices. The system also comprises one or more processors configured to execute a mining module configured to process the field log files stored in the database and identify prominent field usage patterns, and a prediction module configured to predict future workflow patterns by processing the field log files stored in the database. The system further comprises a test case preparation and execution module configured to generate and execute at least one test script for an imaging device based at least in part on the identified usage patterns and the future workflow patterns.

In another disclosed aspect, a method of generating a test script for a medical imaging device comprise receiving field log files comprising data related to examinations performed by one or more imaging devices, processing the field log files and identifying prominent field usage patterns, and constructing and training a long short term memory (LSTM) neural network to identify future workflow patterns. The method further comprises generating and executing at least one test script for testing an imaging device based at least in part on the identified usage patterns and the future workflow patterns.

In another disclosed aspect, a method of predicting future workflow patterns for medical imaging devices comprises identifying all examinations E, performed by a plurality of medical imaging devices, in terms of sequence of scans, constructing a long short term memory (LSTM) Neural Network model for predicting future workflows, and generating a dictionary, D, of scan names and user interface (UI) operations by collecting unique scan names over all examinations. The method further comprises generating a one hot encoding of E by identifying an index of each dictionary word of E in D.

In another disclosed aspect, a system that facilitates generating test cases for execution in imaging devices using information from data log files from a plurality of imaging devices comprises a plurality of imaging devices (120, 122, 124) that generate log files, a log file database (20) that stores the log files, and one or more processors (14) configured to identify workflows comprising sequences of scan operations performed by the imaging devices. The one or more processors are further configured to identify unintended invalid usage patterns and unintended valid usage patterns in the identified workflows, generate test case sequences for at least one of new scan products and scan product updates, and schedule the test case sequences for execution on one or more of the plurality of imaging devices in order to test at least one of the new scan products and scan product updates.

One advantage resides in improved testing ease across a fleet of medical imaging devices.

Another advantage resides in dynamic updating of workflow prediction.

A given embodiment may provide one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
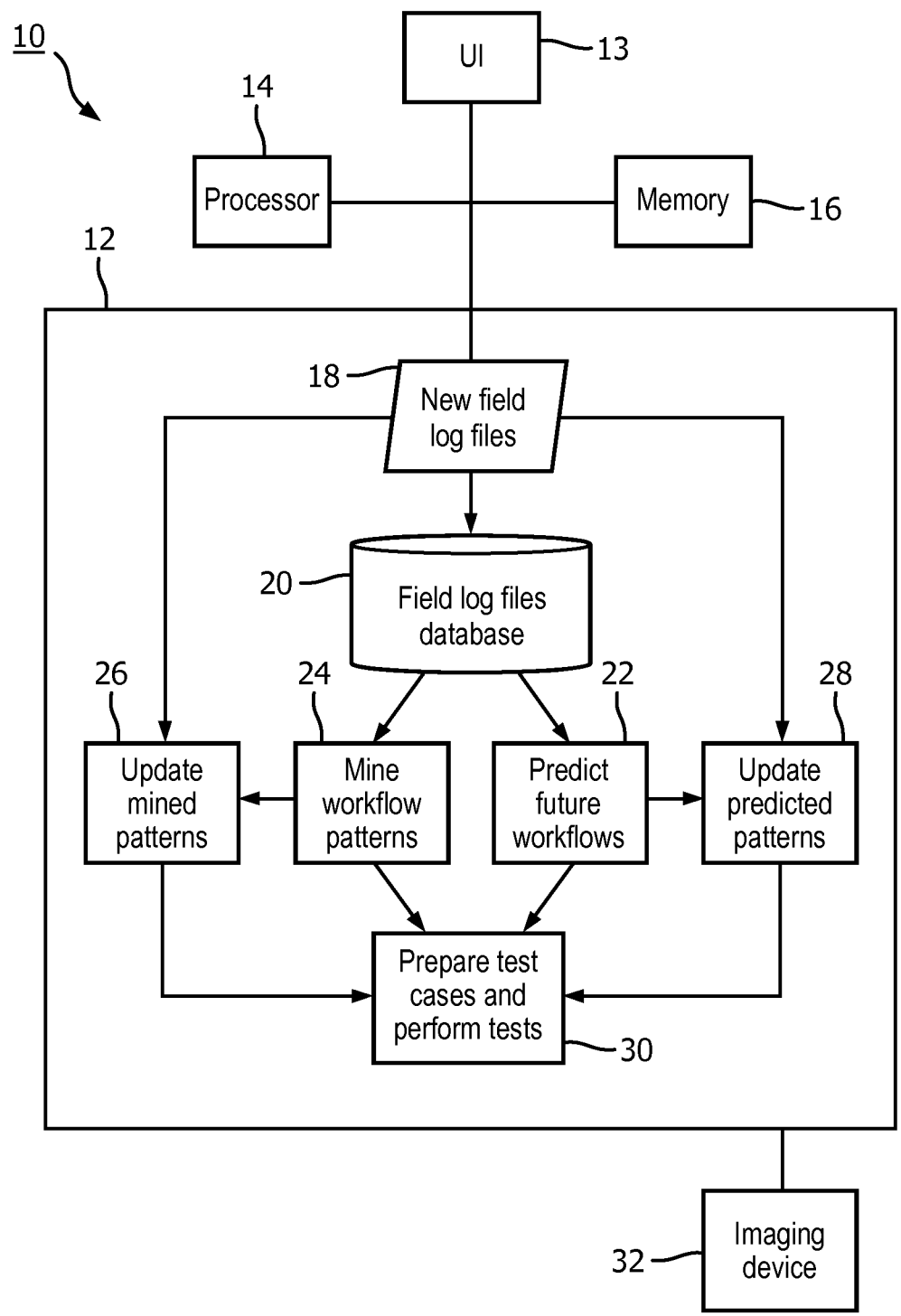
FIG. 1 shows a system that facilitates generating test cases for testing medical imaging devices, in accordance with one or more aspects described herein.

This described systems and methods relate to a testing methodology, which aims to overcome the limitations of the conventional testing methodologies by extensively analyzing the field log files to augment workflows provided in the operational profile with actual workflows followed in hospitals. The approach starts with processing the log files to identify different workflows and derives most important usage patterns by consolidating workflows across the hospitals. The approach further improves the operational profile by predicting possible future variations in currently followed workflows using Machine Learning techniques and adding those predicted profiles to the test system. Additionally, the proposed approach predicts usage of newly introduced product features and generates new operational profiles consisting of those newly introduced product features. Further, the method continuously updates the built Machine Learning model with newly available field logs in real time. In addition, this approach provides a fully automated testing system, which provisions continuous integration of new test cases derived from field logs and the predicted workflows.

Along with generating operational profiles, the described innovation generates usage report of all available scan types, UI operations and other modules of the system. This report includes (without being limited to) extensively used scan types, extensively used UI operations, rarely used scan types, rarely used UI operations, etc. Further, the described innovation generates an extensive performance report of the medical devices. This report includes (without being limited to) CPU usage, memory usage, analysis of time taken for each scan type, analysis of usage time of each UI operations, performance of various machine learning modules, analysis of image quality etc.

The proposed approach addresses the challenges in utilizing field log files to derive prominent usage patterns. Along with identifying most frequent usage pattern, the methodology builds a probabilistic model of usage patterns and explores multiple patterns of varying probabilities. This ensures that derived patterns encompass sparse space of usage patterns. Since the predicted patterns are composed from actual usage patterns, the resultant patterns are expected to align with actual clinical usage of the machine. Further, the methodology builds a Multilayer Neural Network (e.g., long short-term memory (LSTM)) model of usage patterns, which provides multi-fold advantages. Multilayer Neural Network models can learn appropriate weightage to samples in the input sequence irrespective of their input position. Hence, the usage patterns predicted by Multilayer Neural Network efficiently summarize the actual device usage even when there is order inconsistency in device usage.

Additionally, Multilayer Neural Network models have the inherent capability of learning the semantic relationships in the data. This not only enables proposed methodology to predict variations in usage patterns, but also ensures that the predicted patterns align with actual clinical usage of the machine. Further, the proposed approach generates operational profiles consisting of possible unintended usage of medical devices. This is done in two ways. Firstly, by identifying unintended usage in the field by analyzing field log files. Secondly by synthesizing them using aforementioned Multilayer Neural Network and statistical models. Finally, the proposed systems and methods have the capability to generate operational profiles on any subset of data identified using a stratification procedure.

FIG. 1 shows a system 10 that facilitates generating test cases for testing medical imaging devices, in accordance with one or more aspects described herein. The system 10 comprises a test module or device 12 that is coupled to a user interface (UI) 13, processor 14 and memory 16 (i.e., a computer readable medium) and is configured to identify usage patterns for a medical device being tested by the system 10. A "usage pattern," also referred to as a "workflow pattern" herein, is defined as sequence of scans in an exam and parallel user interface (UI) operations performed during the exam.

The processor 14 executes, and the memory 16 stores, one or more computer-executable modules for performing the various functions, methods, etc., described herein. "Module," as used herein, denotes a computer-executable algorithm, routine, application, program, or the like, and/or a processor that executes said computer-executable algorithm, routine, application, program, or the like.

The memory 16 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 14 can read and execute. In this context, the described systems may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

The test module 12 receives new field log files 18 and stores them in a field log file database 20. That is, log files produced from imaging devices, which are installed in hospitals or the like, are stored in field log files database. The stored log files are provided from the database 20 to each of a prediction module 22 that predicts future workflows and a mining module 24 that mines workflow patterns from the log files. New log files 18 are also provided to a mined pattern update module 26 that updates mined workflow patterns based on new input, as well as to a predicted pattern update module that updates patterns predicted by the prediction module 22. A test case preparation module 30 receives input from each of the prediction module 22, the mining module 24, the mined pattern update module 26, and the predicted pattern update module 28, and is configured generate test cases and perform one or more tests on a given imaging device 32.

The prediction module 22 predicts future workflows by processing the log files stored in the database 20 to predict future variations in currently prominent workflow patterns. Log files contain details of different operations performed on the imaging devices. The prediction module first identifies all exams in terms of sequence of scans. Then, the prediction module builds a Multilayer Neural Network model to predict future workflows using the following procedure:

Data Preparation: Let E be collection of all exams, where $i^{th}$ exam Ei is defined as follows:

Ei=Ei1, Ei2, . . . , Eip, for i=1, 2, . . . , n, where Eij is name of $j^{th}$ scan in Ei, ip is number of scans and UI operations in Ei and n is total number of exams in E. The start and the end of the exam are represented as special scans and referred as start scan and end scan respectively. Every exam in E is modified to include start scan and end scan such that Ei1 is start scan and Eip is end scan.

The prediction module 22 generates a dictionary, D, of scan names and UI operations by collecting unique names over all exams, which is defined as follows:

D=D1, D2, . . . , Dl, where Di is $i^{th}$ word in the dictionary and l is number of elements in the dictionary.

Further, the prediction module generates "one hot encoding" of E by identifying an index of each dictionary word of E in D. "One hot encoding" is defined as follows:

OHEdictionary word=[x0, x1, . . . , xn−1], where xi=1 if i=index of dictionary word in D0 otherwise The input tensor, X, and output tensor, y, for LSTM is prepared as follows:

X=X1, X2, . . . , Xn, where $i^{th}$ element Xi is defined as follows:

Xi=OHE(Ei1), OHE(Ei2), . . . , OHE(Eip−1), and y=y1, y2, . . . , yn, where $i^{th}$ element yi is defined as follows:

yi=OHE(Ei2), OHE(Ei3), . . . , OHE(Eip).

Still referring to FIG. 1, the prediction module 22 executes a procedure for predicting workflows using the LSTM model built during Training the Network step as follows:

Let U be input tensor for the LSTM model, which is defined as follows:

U=OHE(U1), OHE(U2), . . . , OHE(Uk), where Ui for i=i to k are input dictionary words and U1=start scan.

Let pred be the LSTM prediction function, which is of the form predU=[V1, V2, . . . , Vk], where each Vi for i=i to k is a vector of class probabilities for each word in the dictionary D.

Let V1=[p0, p1, . . . , pl−1], where p0 is probability of first word in the dictionary, p1 is probability of second word in the dictionary and so on. Let rand(p0, p1, . . . , pl−1) be a random index generator in range (0, l−1) as per given probability distribution p0, p1, . . . , pl−1.

Then, the predicted dictionary words can be derived using following equation:

scanpred$U$=D[randlast element of pred$U$].

Initial input tensor I for prediction is prepared as:

I=[OHEstart scan].

Additionally, predicted exam P is initialized as follows:

P=[start scan].

Predicted scan name for I is given by c=scanpred(I).

Next, I and P are updated using predicted scan name as follows:

I=[I, OHE(c))], and

P=[P, c].

Updated I is further used to predict a next dictionary word. The prediction is repeated until c=end scan. Upon encountering end scan, updated P is recognized as a predicted future workflow. Since the dictionary contains both scan names and UI operations, the predicted future workflow will contain both scan names and UI operations. The foregoing procedure is repeated to obtain multiple future workflows.

The predicted pattern update module 28 updates the Multilayer Neural Network model of usage patterns generated by the prediction module using newly available field log files. The prediction module first identifies all exams in terms of sequence of scans in the new log files. The predicted pattern update module 28 generates a new dataset by combining new exams with exams identified in the stored database log files by the prediction module when predicting future workflows, and follows a procedure similar to that of the prediction module 22 to generate an updated set of the predicted usage patterns.

The mining module 24 processes the log files stored in the database 20 to determine the most prominent field usage patterns. Log files contain details of different operations performed on the medical devices. The mining module 24 first identifies all the exams in terms of sequence of scans and parallel UI operations performed during the exam. Then, the mining module 24 represents identified exams in a tree data structure. Each scan of an exam is represented as a node in the tree and transition from one scan to the other scan is represented as an edge in the tree. Each node stores a count of encountering the node while populating the tree. The start and the end of the exam are represented as special nodes in the tree and referred as start node and end node respectively. Further, the mining module 24 stores UI operations performed during the exam on the end node. After populating the tree with all the exams in the log file database, the count stored in the end node will represent the count of a specific exam present in the log file database. Then, the mining module 24 generates two sets of prominent usage using the following procedures, which are referred to as Procedure 1 and Procedure 2.

Procedure 1: This procedure identifies most commonly used exams and suggests them as prominent usage pattern using following procedure: Let Ci be the count stored on $i^{th}$ end node. Then $k^{th}$ most prominent pattern is defined as follows:

Ek=[Ek0, Ek1, . . . , Ekn], for k=1, 2, . . . , where Ek0 is start node, Ekn is $k^{th}$ most occurring end node.

Procedure 2: This procedure generates a probabilistic model of usage patterns and identify the most prominent field usage patterns using the following procedure: Let Cij be the count stored in the $j^{th}$ child node of $i^{th}$ node of the tree. Then, Pij the probability of transiting from $i^{th}$ node to $j^{th}$ child of $i^{th}$ node is defined as follows:

Pij=CijSi where Si=Cij and n is number of child nodes of $i^{th}$ node.

Further, $k^{th}$ most prominent pattern is defined as follows:

Ek=[Ek0, Ek1, . . . , Ekn], for k=1, 2, . . . , where Ek0 is start node, Ekn is end node, Ek1 is $k^{th}$ most probable child node of Ek0 and so on.

The mined pattern update module 26 updates the probabilistic models of the usage patterns generated by the mining module 24 when mining workflow patterns, using newly available field log files 18. The mined pattern update module 26 first identifies all exams in terms of sequence of scans and parallel UI operations performed during the exam in the new log files 18. Then, the mined pattern update module 26 generates a new dataset by combining new exams with exams identified by the mining module 24 when mining workflow patterns and follows a procedure similar to that executed by the mining module, in order to generate updated prominent field usage patterns.

The test case preparation module 30 generates test scripts using usage patterns identified by the other modules, performs the tests on an imaging device, and generates test reports.

Figure 2:
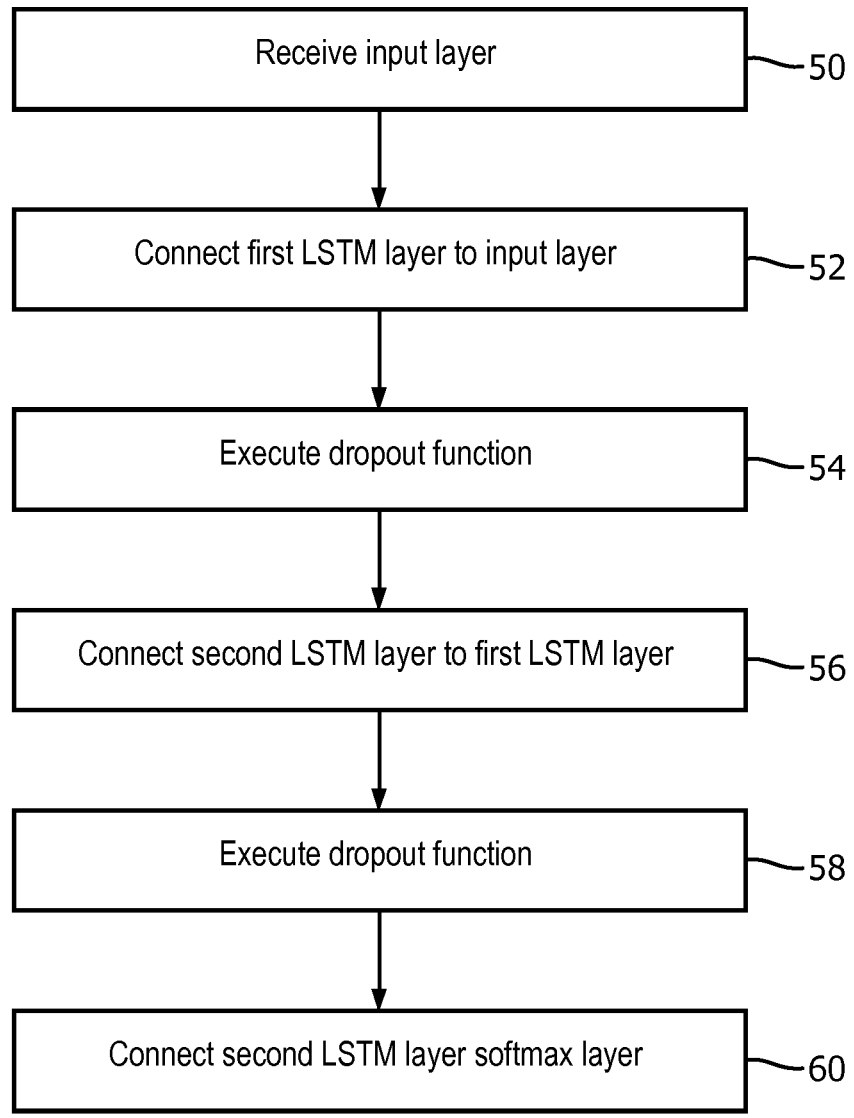
FIG. 2 illustrates a method for generating the herein-described neural network, in accordance with one or more aspects described herein.

With continued reference to FIG. 1, FIG. 2 illustrates a method for generating the herein-described neural network, such as can be performed by the prediction module 22 of FIG. 1, in accordance with one or more aspects described herein. A multilayer long short-term memory (LSTM) network is constructed using two (or more) layer LSTM as shown FIG. 2. However, it will be appreciated that more or fewer layers may be employed when constructing the neural network. Input tensor X is received as input layer at 50. The input layer is densely connected to first LSTM layer at 52. LSTM layers are made up of one or more LSTM cells. Each LSTM cell contains three gates namely input gate, forget gate and output gate, equation for which is given below.

$$i(t)=g[W_{xi}X(t)+W_{hi}H(t-1)+B_i], \text{ for } t=0,1,2,\ldots,$$

$$f(t)=g[W_{xf}X(t)+W_{hf}H(t-1)+B_f], \text{ for } t=0,1,2,\ldots,$$

$$o(t)=g[W_{xo}X(t)+W_{ho}H(t-1)+B_o], \text{ for } t=0,1,2,\ldots,$$

where i(t) is input gate, f(t) is forget gate and o(t) is output gate activation at time t, Wx are weights and B are bias, X(t) is input at time t and H(t−1) is cell output at the previous time step. Input is transformed by tanh as shown below.

$$c\_in(t)=\tanh(W_{xc}X(t)+W_{hc}H(t-1)+B_{c\_in}), \text{ for } t=0,1,2,\ldots,$$

where c_in(t) is transformed input, Wx are weights and B are bias, X(t) is input at time t and H(t−1) is cell output at the previous time step. Further, hidden states are updated as follows.

$$c(t)=f(t)*c(t-1)+i(t)*c\_in(t), \text{ for } t=0,1,2,\ldots,$$

$$h(t)=o(t)*\tanh(c(t)), \text{ for } t=0,1,2,\ldots,$$

Here * is element wise product operation and c(t−1) is cell activation at previous time step and h(t) is cell output at time t. At 54, a dropout function is applied to the first LSTM layer to improve network regularity. The dropout function ignores a fraction of network nodes and corresponding activations during training. Dropout function chooses a new set of nodes at random with replacement at every training iteration. At 56, a second LTSM layer is densely connected to the first LSTM layer, the dropout function is applied to the second LSTM layer at 58. Thus, each LSTM layer is further densely connected to the next level LSTM layer and dropout function is applied to further improve network regularization. The last LSTM layer is densely connected to a "softmax" output layer, at 60. The softmax function is given below:

$$S(Z)_j = \frac{\exp(Z_j)}{\sum_{k=1}^{K} \exp(Z_k)}, \text{ for } j = 1, 1, 2, \ldots K,$$

where Z is K dimensional input to the function and exp is exponentiation function.

Figure 3:
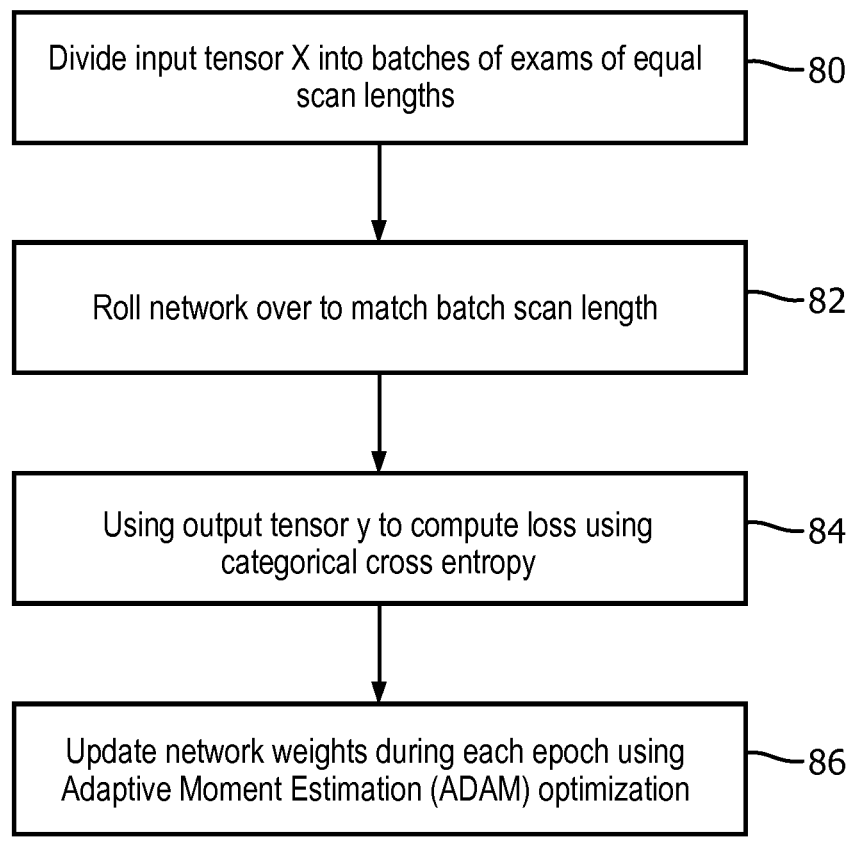
FIG. 3 illustrates a method for training the neural network, in accordance with one or more features described herein.

FIG. 3 illustrates a method for training the neural network, in accordance with one or more features described herein. When training the network, the input tensor X is divided into batches of exams of equal scan lengths, at 80. Then, during training the network is rolled over to match batch scan length, at 82. Here, roll over refers to process of replicating LSTM cells to match input length, such that all the such replicated cells use same copy of the network weights and biases. Categorical cross entropy is used as loss function, which makes use of the output tensor y to compute the loss, at 84. Categorical cross entropy is defined below:

$$H(p, y) = -\sum_{x} p(x)\log(y(x)),$$

where p is true distribution. However, it will be appreciated that several other loss functions (for example mean squared error, Kullback Leibler Divergence etc.) may be employed when constructing the neural network. Further, Adaptive Moment Estimation (ADAM) optimization is used to update network weights during each epoch (i.e., one forward pass and one backward pass over all training examples), at 86. However, it will be appreciated that several other optimization functions (for example Stochastic gradient descent, RMSprop, Adagrad etc.) may be employed when training the neural network.

Figure 4:
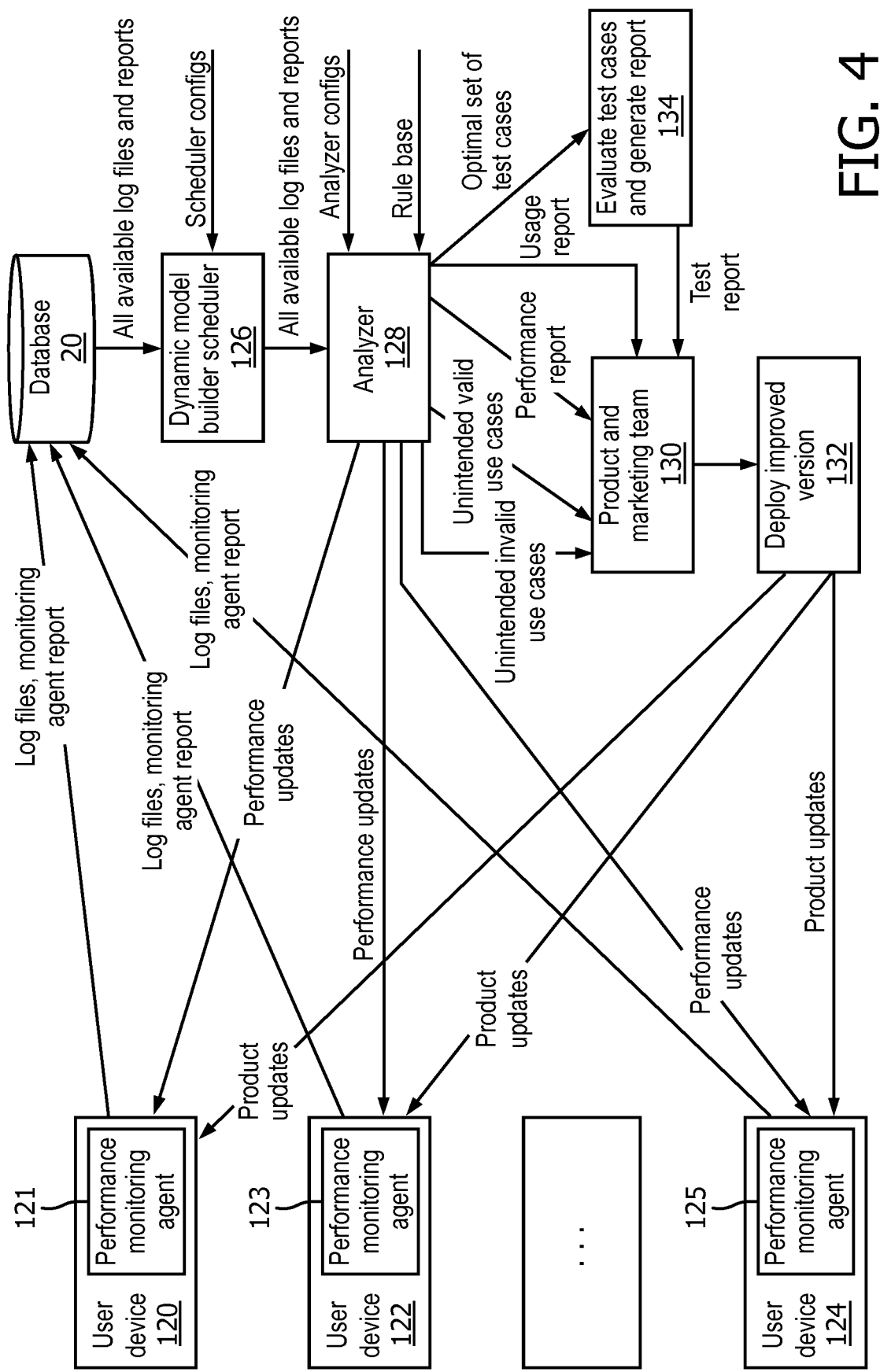
FIG. 4 illustrates a block diagram showing detailed aspects of the innovation, in accordance with one or more features described herein.

FIG. 4 illustrates a block diagram showing detailed aspects of the innovation, such as may be comprised by the system 10 of FIG. 1 and executed by the processor 14, in accordance with one or more features described herein. The database 20 receives and stores log files and monitoring agent reports from each of a plurality of user devices 120, 122, 124 (i.e., medical imaging devices), each of which comprises a respective performance monitoring agent 121, 123, 125. A dynamic model builder scheduler module 126 receives all available log files and reports from the database 120, as well as scheduler configuration information for scheduling test cases. An analyzer module 128, executable by the processor 14 (FIG. 1), receives all available log files and reports from the scheduler module 126, in addition to analyzer configuration information and a rule base via which rules are defined for performing analysis. The analyzer transmits performance updates to each of the user devices 120, 122, 124. In one or more embodiments, the analyzer module performs the functions of the mining module 24 and/or the future workflow prediction module 22 of FIG. 1. In this regard, the mining module and/or future workflow prediction modules of FIG. 1 can be considered to include the analyzer of FIG. 4, such that all functions, procedures, methods, etc., carried out by the analyzer module 128 can similarly be performed by the mining module 24 and/or the future workflow prediction module 22.

The analyzer 128 also identifies and transmits to a product marketing server 130 additional information including but not limited to unintended invalid use cases, unintended valid use cases, performance reports, usage reports, etc., for imaging devices being analyzed. Based on this information, the product and marketing server 130 deploys one or more improved product versions 132, which are transmitted as product updates to the user devices. Additionally, the analyzer 128 transmits a set of selected optimal test cases to an evaluation team server 134 for evaluation of test cases and generation of a test report that is provided to the product and marketing server 130 for improving product versions.

Figure 5:
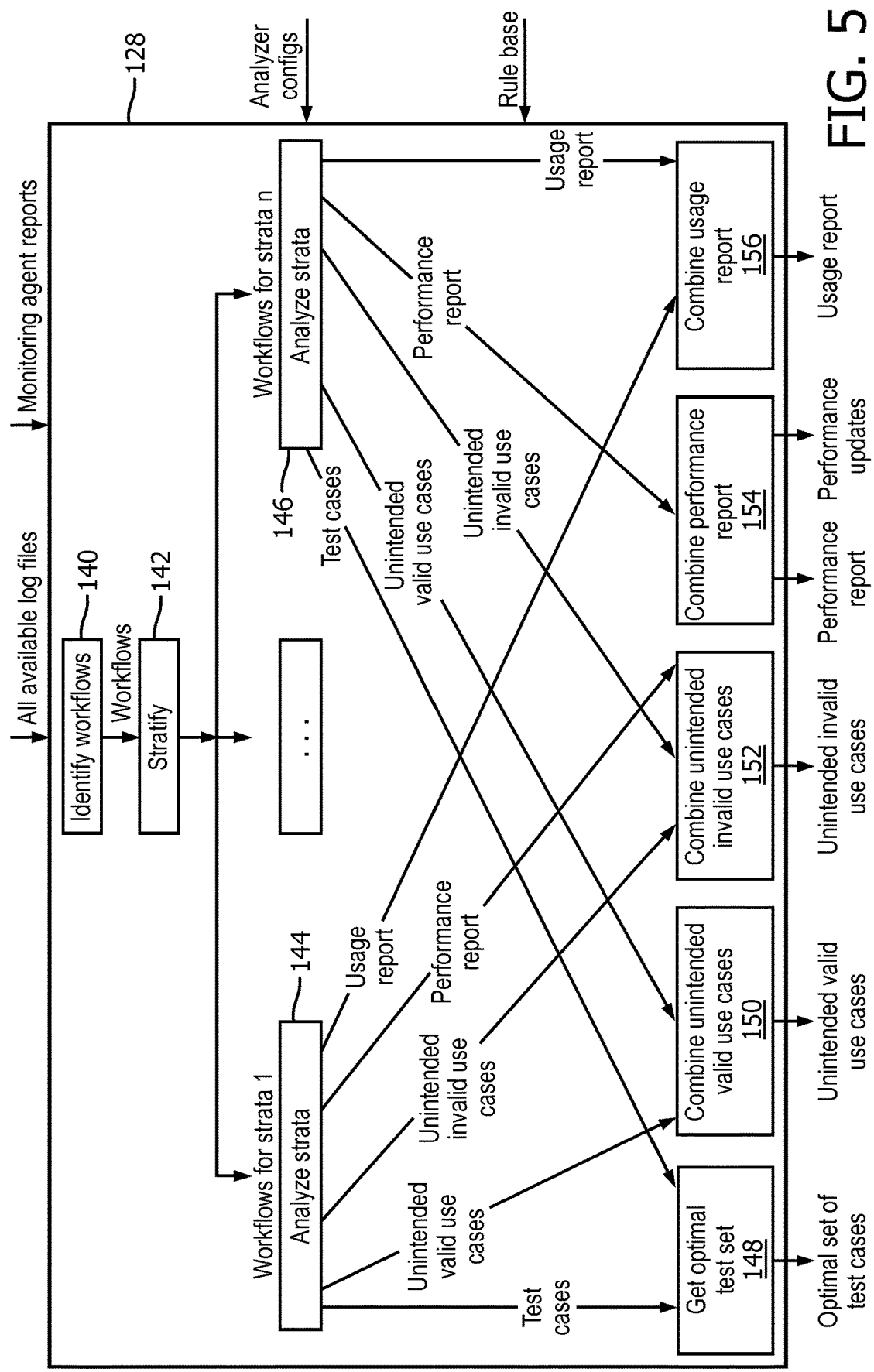
FIG. 5 diagrammatically shows various aspects of the analyzer module, in accordance with one or more aspects described herein.

FIG. 5 diagrammatically shows various aspects of the analyzer module 128, in accordance with one or more aspects described herein. The analyzer module receives all available log files and monitoring agent reports and a workflow identification module 140 identifies workflows therefrom and provides the identified workflows to a stratification module 142. Strata workflows are analyzed by a plurality of strata analysis modules, including a first strata analysis module 144 that analyzes a first strata workflow through an nth strata analysis module 146 that analyzes an nth strata workflow. Each strata analysis module 144, 146 generates test cases that are provided to a test set optimizer module 148 that generates and outputs an optimal test set based on one or more predefined criteria. Each strata analysis module 144, 146 identifies unintended valid use cases and provides them to a valid use case combiner module 150 that combines and outputs the unintended valid uses cases. Unintended invalid use cases are also identified by the strata analyzer modules and transmitted to an invalid use case combiner module 152 that combines and outputs the unintended invalid uses cases. Performance reports are provided by the strata analyzers to a performance report combiner module 154 that combines and outputs performance reports. Additionally, usage reports are provided by the strata analyzers to a usage report combiner module 156 that combines and outputs usage reports.

Figure 6:
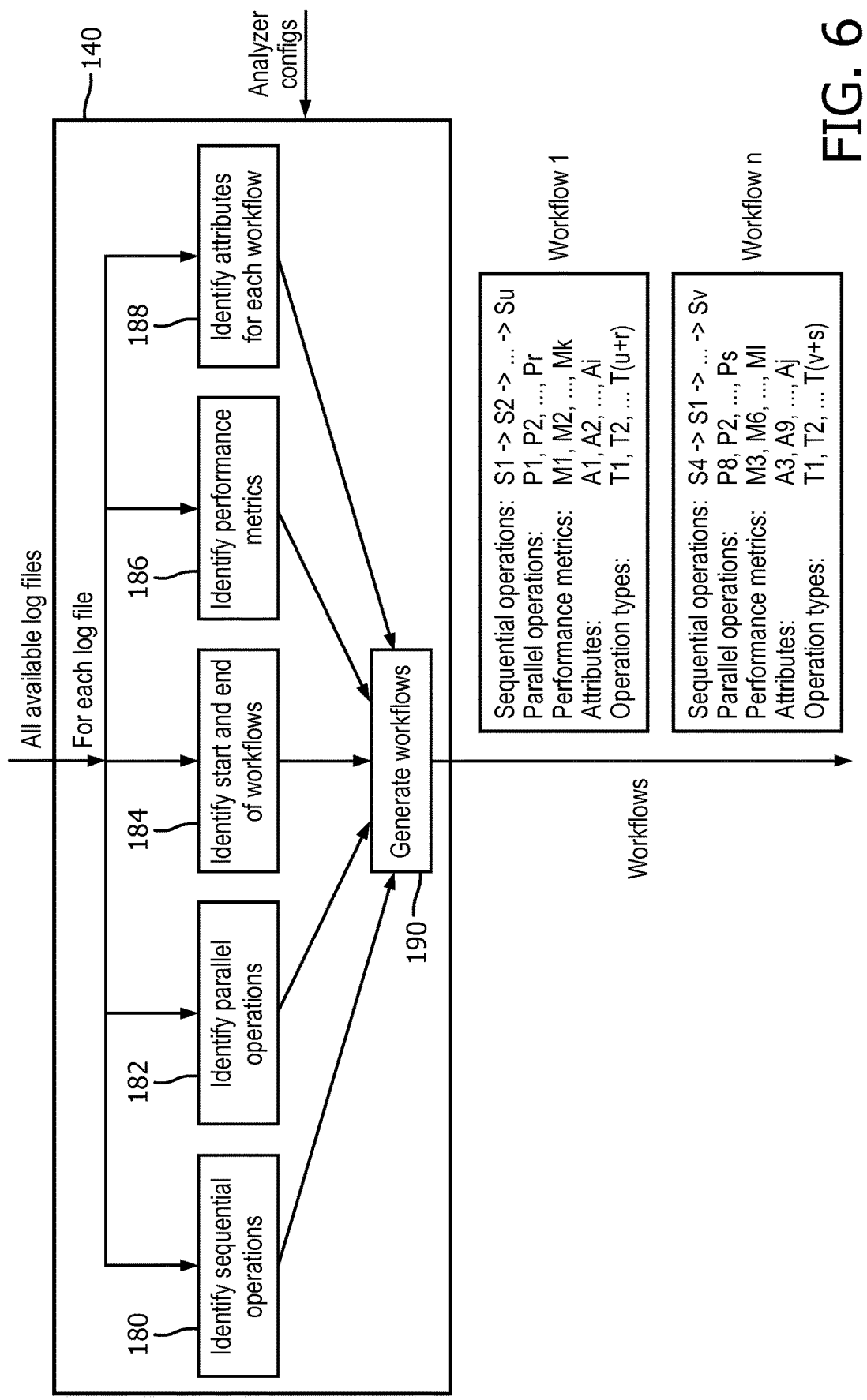
FIG. 6 shows a method of identifying workflows, in accordance with one or more aspects described herein.

FIG. 6 shows a method of identifying workflows such as is performed by the workflow identification module 140 when executed by a processor (e.g., the processor 14 of FIG. 1), in accordance with one or more aspects described herein. The workflow identification module receives all available log files as well as analyzer configuration information. For each log file, the workflow identification module 140 identifies sequential operations at 180, parallel operations at 182, a start and end of each workflow at 184, performance metrics at 186, and attributes for each workflow at 188. From these identified pieces of information, the workflow identification module 140 generates and outputs one or more workflows, at 190.

Figure 7:
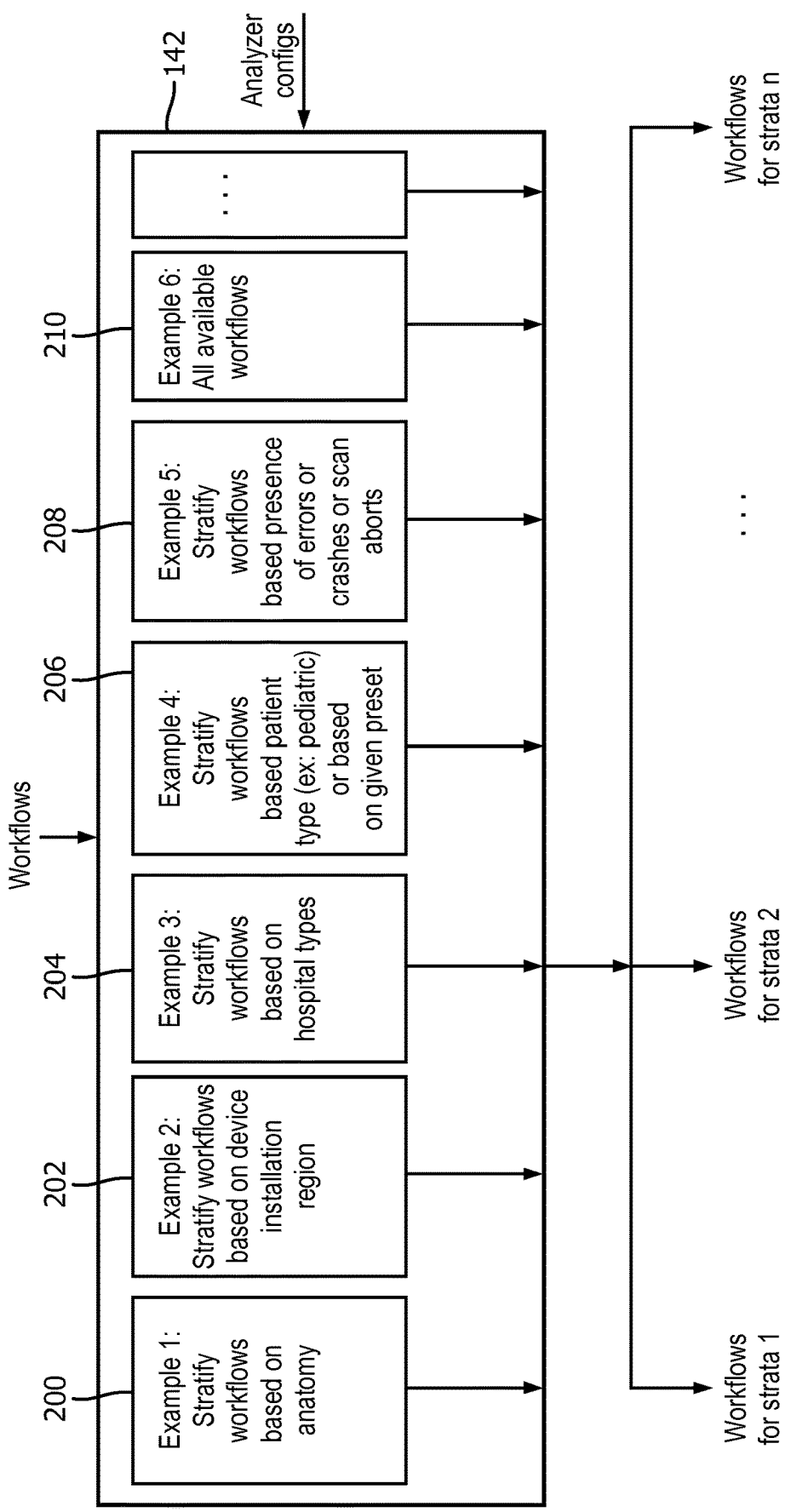
FIG. 7 shows various examples of criteria via which the workflows can be stratified, in accordance with one or more aspects described herein.

FIG. 7 shows various examples of criteria via which the workflows can be stratified by the stratification module 142, in accordance with one or more aspects described herein. The stratification module receives the workflows generated by the workflow identification module 140 (FIG. 6), as well as analyzer configuration information, and stratifies the workflows based on one or more criteria or parameters, which may be specified in the analyzer configuration information. In a first example, workflows are stratified based on anatomy, such as the anatomical regions of patients being imaged using the respective workflows. In a second example, workflows are stratified based on a region in which the devices using the respective workflows are installed (e.g., a physical location or region, hospital or department, etc.). In a third example, workflows are stratified based on the type of hospitals in which they are employed (e.g., a surgery center, a cancer center, etc.). In a fourth example, workflows are stratified based on patient type (e.g., pediatric, geriatric, etc.) or based on a given preset. In a fifth example, workflows are stratified based on a presence of one or more of errors, crashes, scan aborts, or the like detected in devices using the workflows. In another example, all available workflows are passed through without stratification, if indicated by the analyzer configuration information. In any event, workflows for each stratum (1, 2, . . . , n) are output.

Figure 8:
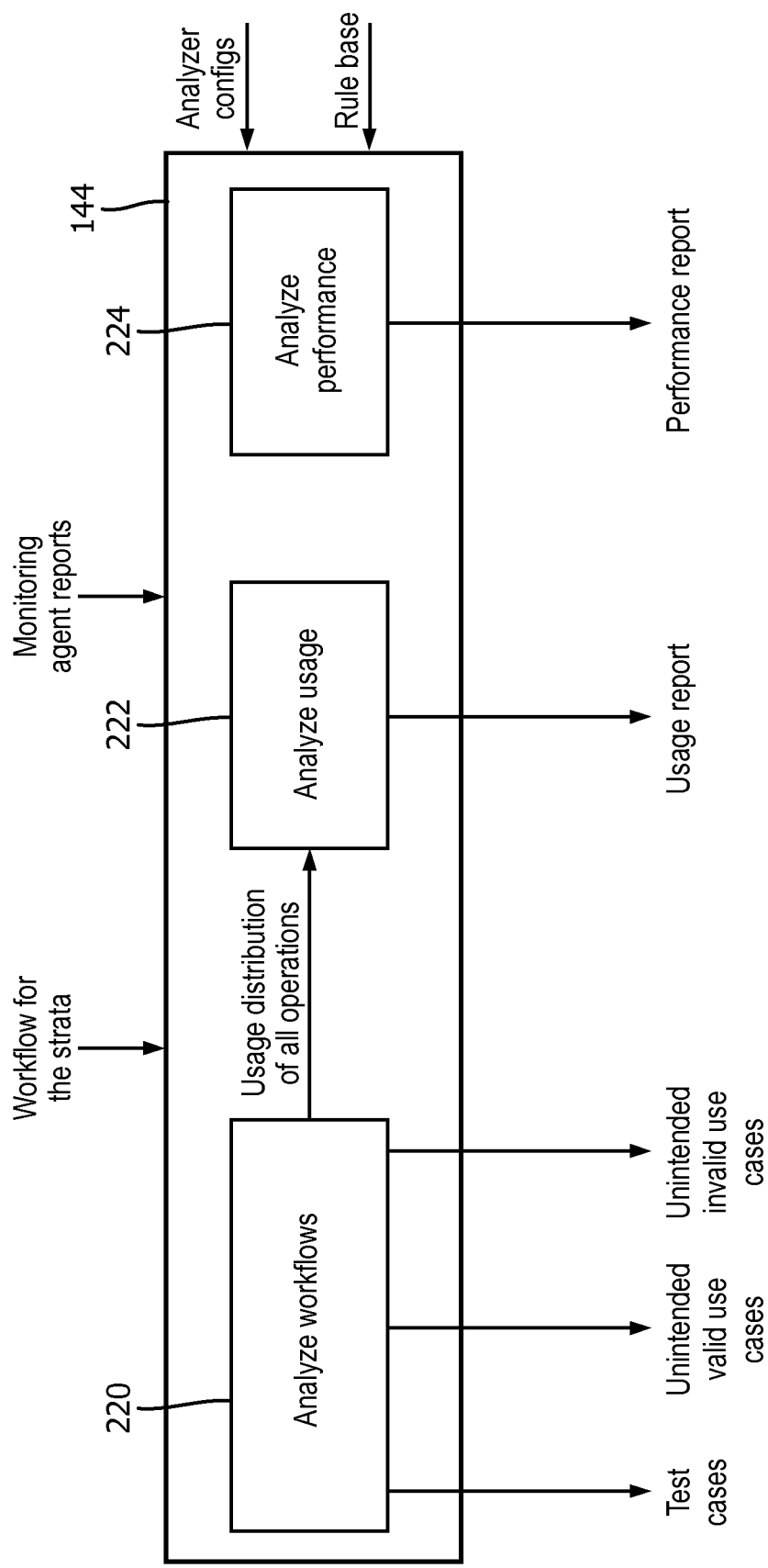
FIG. 8 shows a method for analyzing strata workflows, such as the processor 14 (FIG. 1), in accordance with one or more aspects described herein.

FIG. 8 shows a method for analyzing strata workflows such as may be performed by the strata analysis module(s) 144 (and 146) when executed by a processor, such as the processor 14 (FIG. 1), in accordance with one or more aspects described herein. The stratified workflows output by the stratification module 142 are received by the strata analysis modules, along with monitoring agent reports, analyzer configuration information, and rule base information that defines one or more rules for analyzing the strata workflows. Workflow analysis is performed at 220 to identify and output test cases, unintended valid use cases, and unintended invalid use cases. Additionally, usage distribution information for all operations included in the workflows of the strata is output and usage analysis is performed at 222 to generate and output usage reports. Performance analysis is also performed at 224 to generate and output performance reports describing performance of workflows and/or imaging devices employing the workflows.

Figure 9:
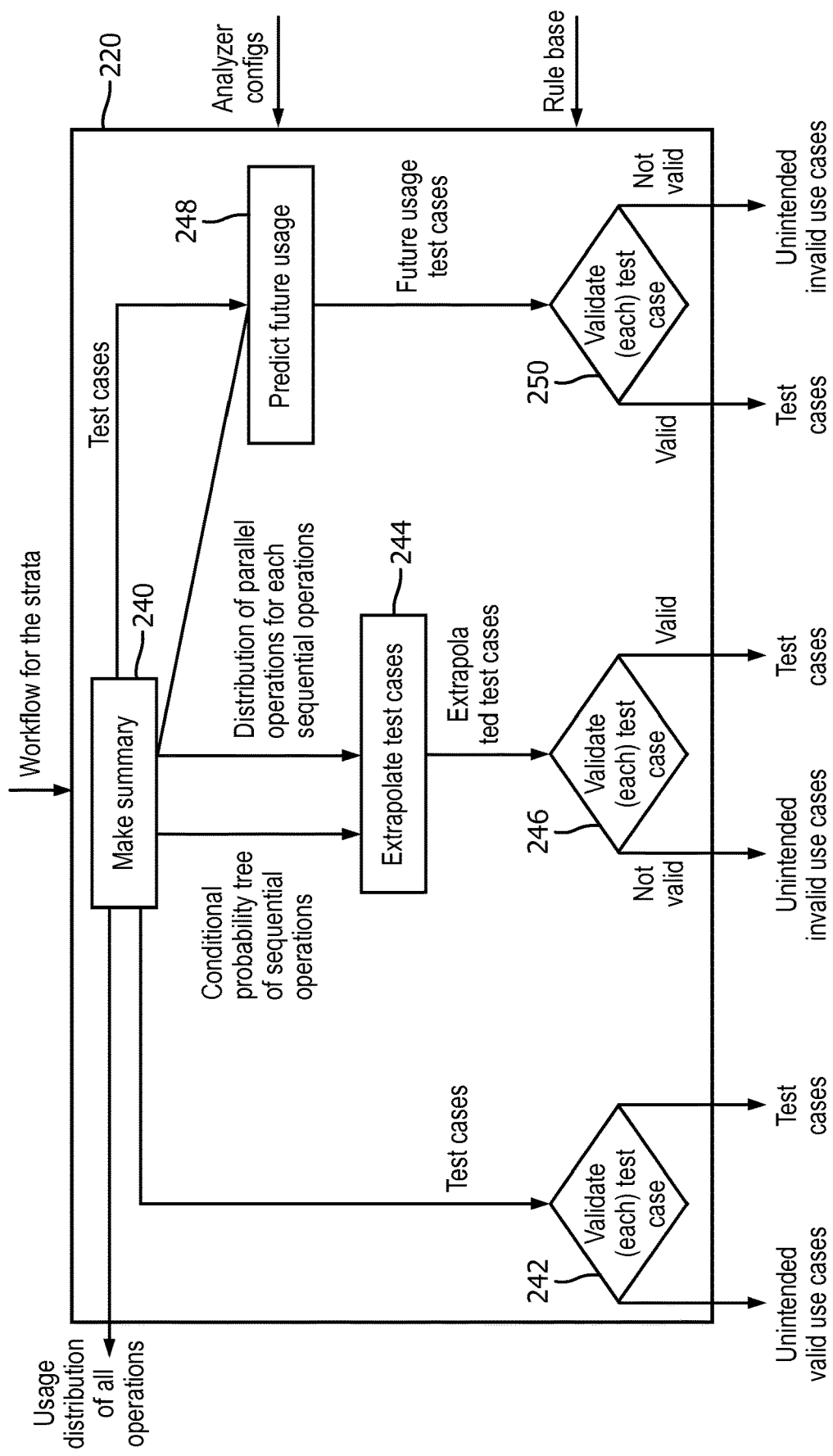
FIG. 9 illustrates a method for analyzing workflows, in accordance with one or more aspects described herein.

FIG. 9 illustrates a method for analyzing workflows, such as may be carried out by the workflow analysis module 220 when executed by a processor (such as the processor 14 of FIG. 1), in accordance with one or more aspects described herein. Workflow for a given workflow stratum is received by the workflow analysis module 220. At 240, the workflow analysis module generates a summary of the workflow. The summary comprises, as output, usage distribution information for all operations within the workflows comprised by the stratum. At 242, a determination is made regarding whether identified test cases are valid using the Rule Base. Test cases that are practiced in the field (and generated by mining log files) but not validated according to the Rule Base are considered unintended valid test cases. Test cases that are practiced in the field and get validated according to the Rule Base are output as valid test cases.

At 244, test case extrapolation is performed. This step may be similar or identical to the actions performed by the mining module 24 (FIG. 1). Test case extrapolation can be carried out using, e.g., a conditional probability tree of sequential operations (i.e., operations carried out in a sequence during a workflow), as well as a distribution of parallel operations for each sequential operation. At 246, a determination is made regarding whether extrapolated test cases are valid according to the Rule Base. Invalid cases are output as unintended invalid use cases, while extrapolated test cases that are valid according to the Rule Base are output into the pool of valid test cases.

Additionally, identified test cases at 240 can be analyzed, at 248, in order to generate future usage test cases. This step may be similar or identical to the actions performed by the future workflow prediction module 22 (FIG. 1). At 250, a determination is made regarding whether predicted future usage test cases are valid according to the Rule Base. Invalid test cases are output as unintended invalid use cases, while predicted future usage test cases that are valid according to the Rule Base are output into the pool of valid test cases.

Figure 10:
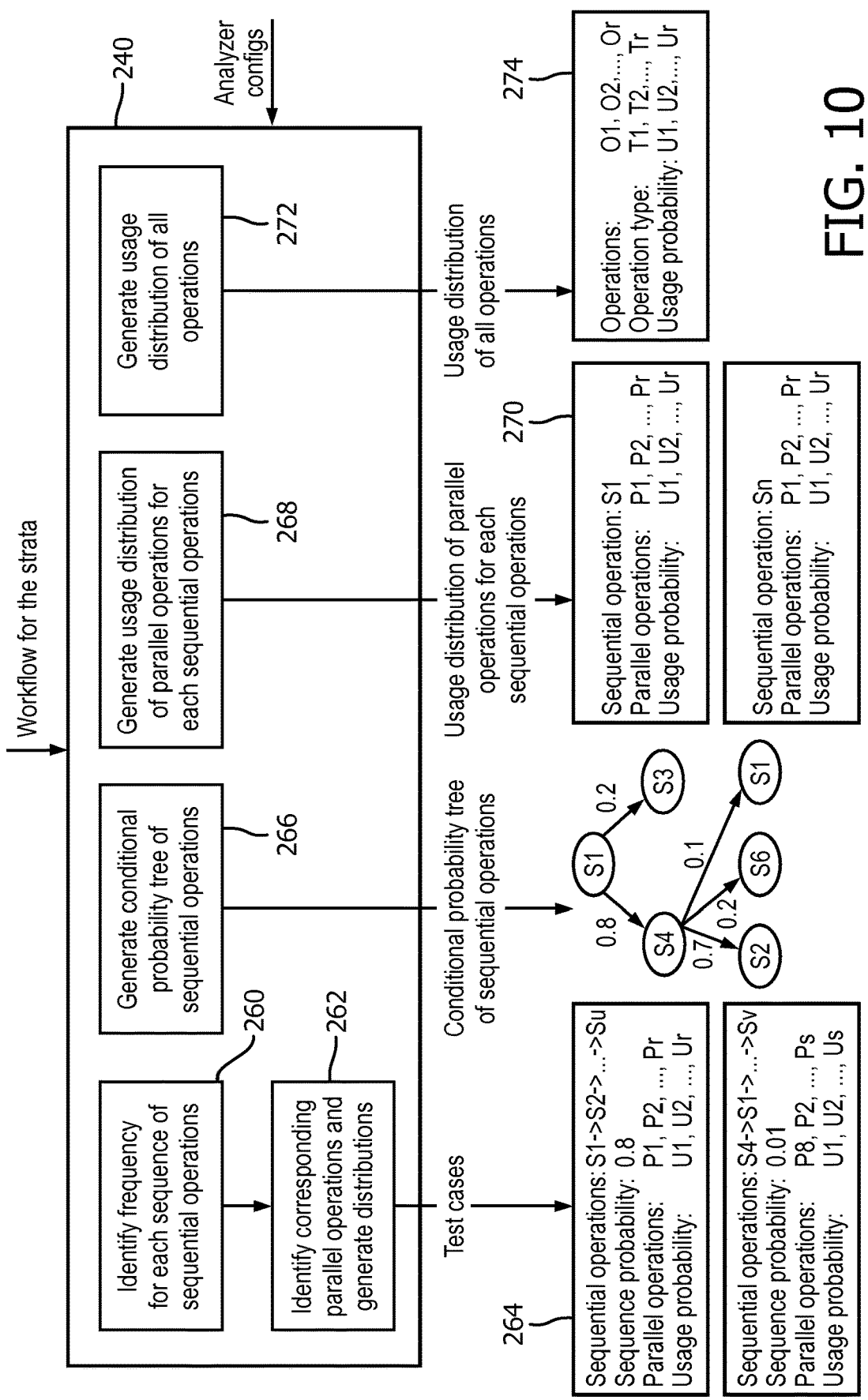
FIG. 10 illustrates a method for generating workflow summaries.

FIG. 10 illustrates a method for generating workflow summaries such as is performed by the workflow analysis module 220 as described with regard to FIG. 9. The workflow analysis module receives one or more workflows for a given strata as well as analyzer configuration information, and, at 260, identifies a frequency for each sequence of sequential operations carried out in each workflow. At 262, corresponding parallel operations are identified for each sequential operation and distribution information is generated for test cases 264 output by the workflow analysis module.

Concurrently, at 266, a conditional probability tree is generated to represent probabilities for sequential operations pathways in the strata workflow. Sequential operations are identified in nodes S with probabilities represented as edges in the tree. Additionally, at 268, usage distribution information 270 is generated for parallel operations for each sequential operation. At 272 usage distribution information 274 for all operations (parallel and sequential) is generated and output.

Figure 11:
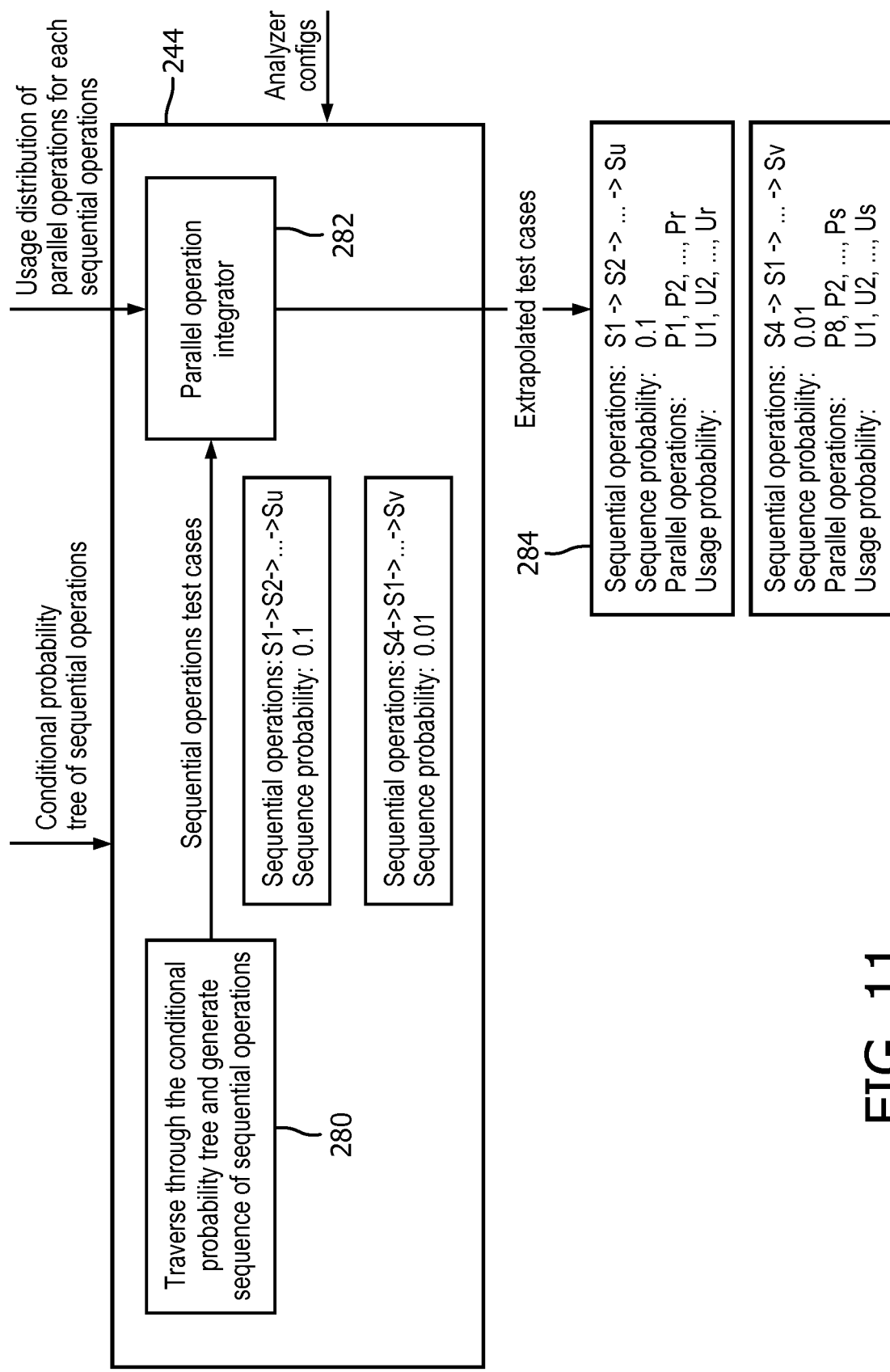
FIG. 11 shows a method for extrapolating test cases, in accordance with one or more features described herein.

FIG. 11 shows a method for extrapolating test cases, such as can be performed at step 244 of FIG. 9 by the workflow analysis module 220 in accordance with one or more features described herein. After receiving information related to the conditional probability tree of sequential operations, the usage distribution of parallel operations for each sequential operation, and analyzer configuration information, at 280 the workflow analysis module 220 traverses the conditional probability tree and generates a sequence of sequential operations to form test cases. Parallel operation integration is performed using the usage distribution of parallel operations for each sequential operation, at 282, to generate extrapolated test cases 284.

Figure 12:
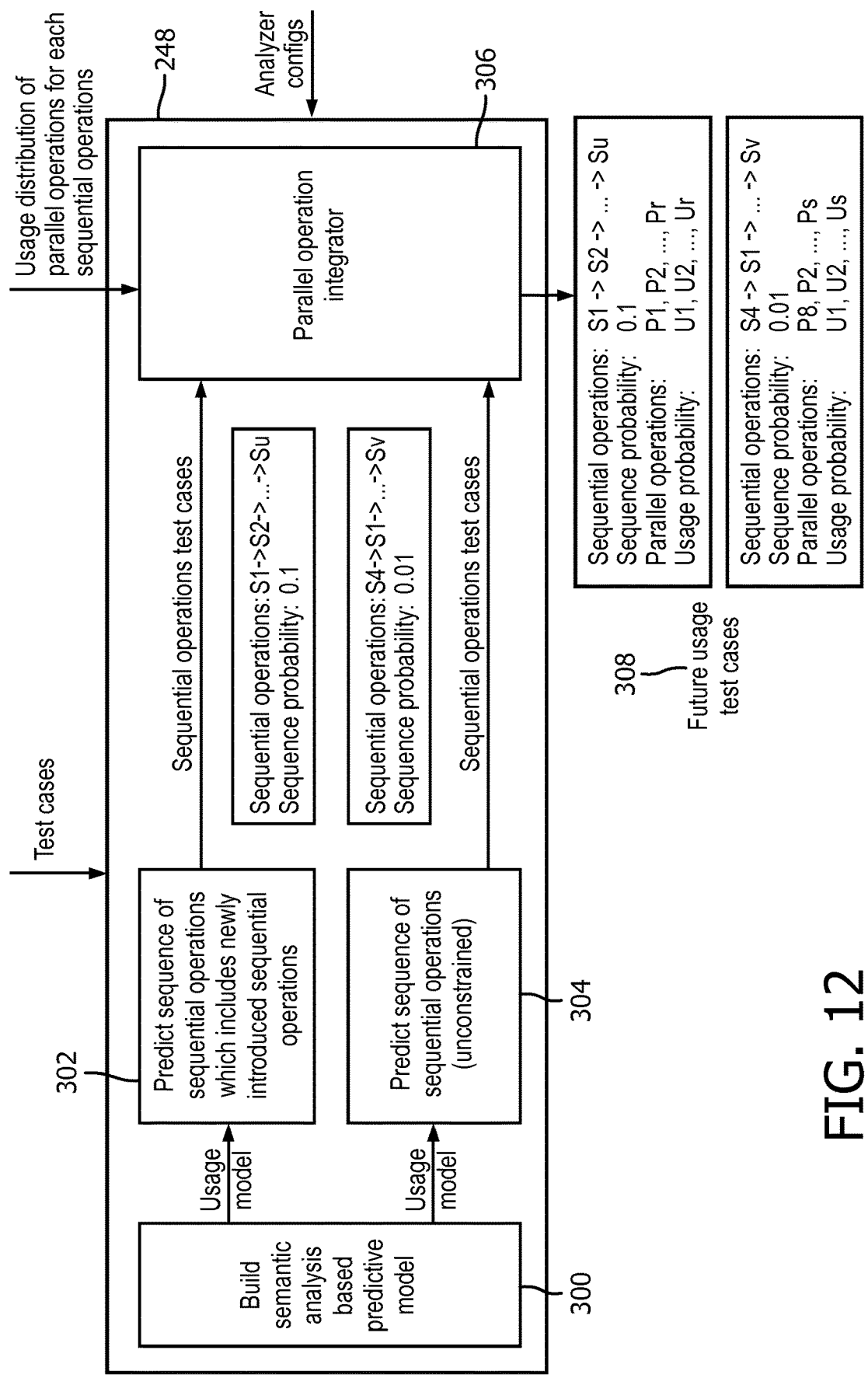
FIG. 12 shows a method for predicting future usage test cases, in accordance with one or more features described herein.

FIG. 12 shows a method for predicting future usage test cases, such as can be performed at step 248 of FIG. 9 by the workflow analysis module 220 in accordance with one or more features described herein. After receiving information related to the identified test cases at 240, the usage distribution of parallel operations for each sequential operation, and analyzer configuration information, at 300 the workflow analysis module 220 builds and outputs a predictive usage model based on semantic analysis of the workflows. According to an example, when a new scan type is introduced for a given imaging modality, there may be few usage examples of the scan type from the field. Semantic analysis model facilitates prediction of future usage of the new scan type based on the usage of similar scan types (e.g., scan types with similar parameters) without requiring rewriting of specific rules.

At 302, a sequence of sequential operations is predicted using the usage model and includes newly introduced sequential operations, in order to generate sequential operations test cases. Concurrently, at 304, sequences of sequential operations are predicted in an unconstrained manner (i.e., including all sequential operations and not just newly introduced sequential operations) to generate additional sequential operations test cases. At 306, parallel operation integration is performed on the sequential operations test cases generated at 302 and 304, in order to generate and output future usage test cases 308.

Figure 13:
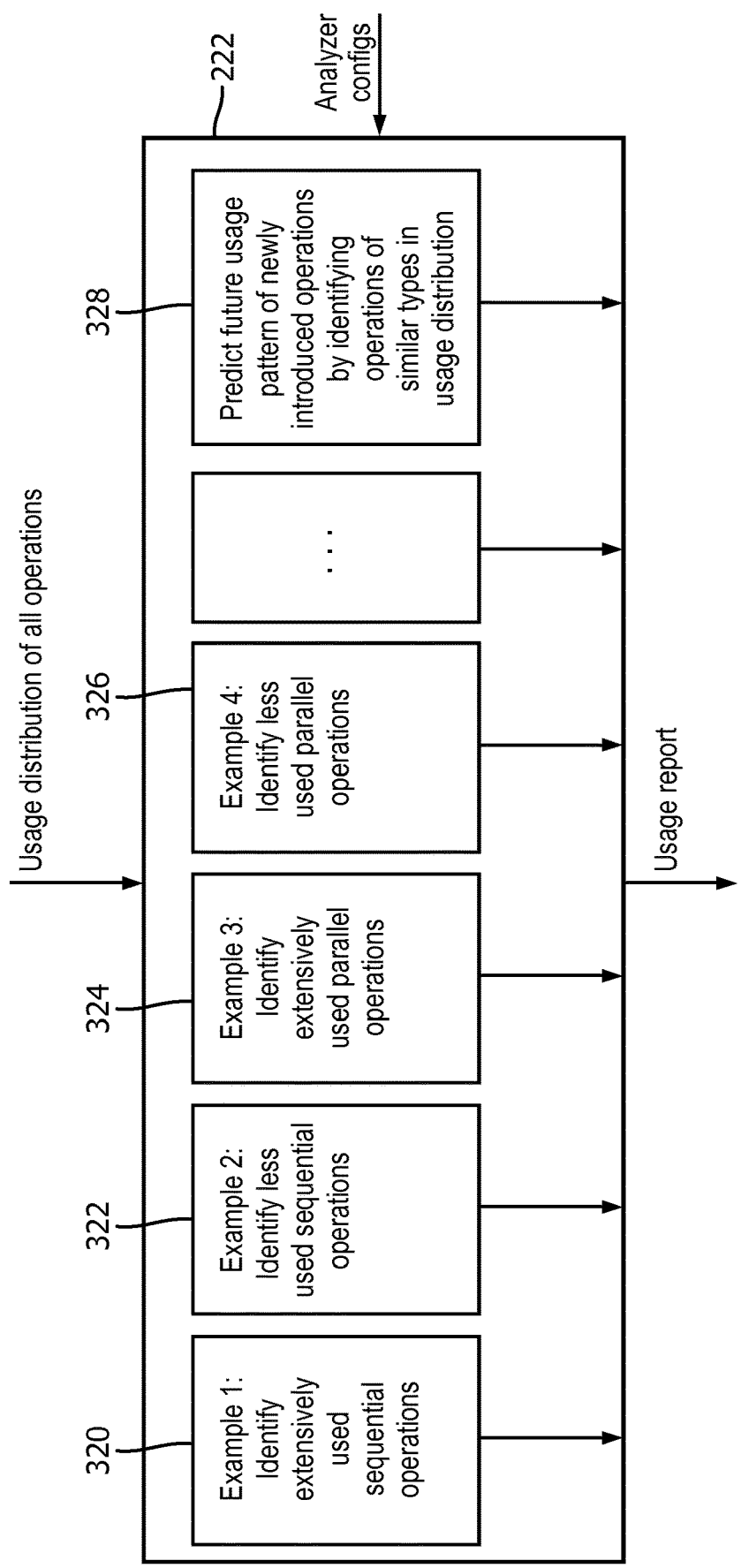
FIG. 13 shows a method of generating a usage report, in accordance with one or more features described herein.

FIG. 13 shows a method of generating a usage report such as is output by the strata analysis module 144 of the analyzer module 128 to the product and marketing server 130 of FIG. 4, in accordance with one or more features described herein. At 320, extensively-used sequential operations are identified. In one embodiment, "extensively-used" denotes usage above a first predefined threshold level (e.g., 20% of workflows, 40% of workflows, or some other predefined threshold level). At 322, less-used sequential operations are identified. In one embodiment, "less-used" denotes usage below the first predefined threshold level. At 324, extensively-used parallel operations are identified. Extensive use of parallel operations may be defined as being above the first threshold used for extensively-used sequential operations or a different (second) threshold level. At 326, less used parallel operations are identified. Lesser use of the parallel operations may be defined as use below the threshold used to identify extensively-used parallel operations.

Additionally, at 328, future usage patterns of newly introduced operations are predicted by identifying operations of similar types in the usage distribution. For instance, when a new scan type or user interface is introduced for a given imaging device, the strata analysis module 144 uses the usage distribution information to predict future usage patterns for the scan type or user interface based on usage of similar operation types, before the new scan type or user interface is release to the market as a new build version. It will be understood that any two or more of the steps performed during usage analysis may be performed in parallel (concurrently) or sequentially (in any desired order) in order to generate and output a usage report.

Figure 14:
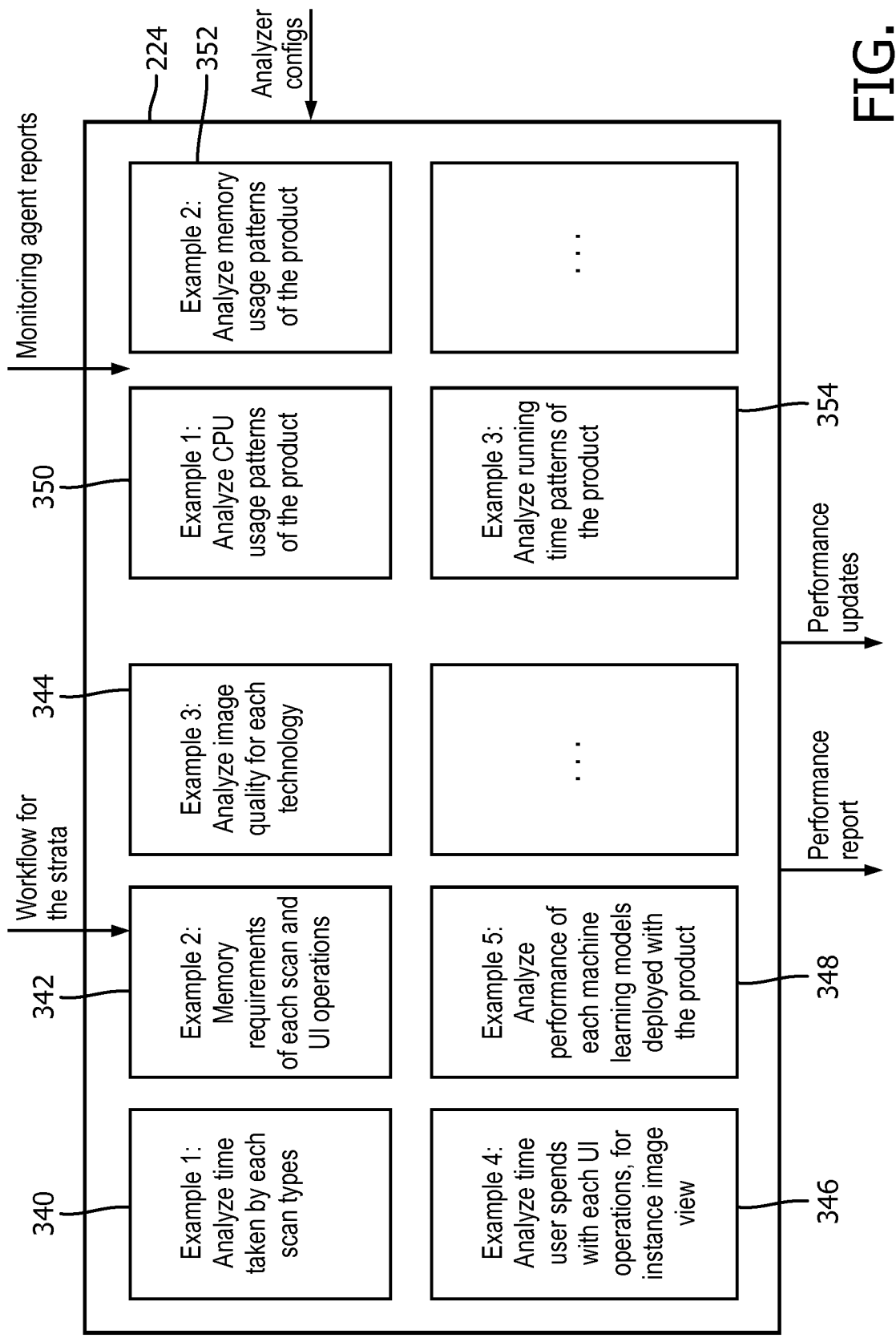
FIG. 14 shows a method for analyzing performance such as can be performed by the strata analysis module(s), in accordance with one or more features described herein.

FIG. 14 shows a method for analyzing performance such as can be performed at step 244 (FIG. 9) by the strata analysis module(s) 144 (and 146) (see, e.g., FIG. 5), in accordance with one or more features described herein. Examples of parameters that can be analyzed to generate performance reports and/or updates are provided. After receiving strata workflow information, at 340 an amount of time required to perform each of a plurality of scan types is analyzed and/or computed. At 342, memory requirements for each scan and/or UI operation is analyzed and/or computed. At 344, image quality for each imaging modality used is analyzed and/or computed. At 346, an amount of time spent by a user with each of a plurality of UI operations is analyzed and/or computed. At 348, performance of each of a plurality of machine learning models deployed with a given product is analyzed and/or computed. Any or all of the foregoing analyses and/or computations can be included in a performance report output by the strata analysis modules described herein.

After receiving one or more reports from the performance monitoring agents 121, 123, 125 (FIG. 1), at 350 processing (CPU) usage patterns for a given product are analyzed and/or computed. At 352, memory usage patterns for the given product are analyzed and/or computed. At 354, run time patterns for the given product are analyzed and/or computed. Any or all of the foregoing analyses and/or computations can be included in a performance update(s) output by the strata analysis modules described herein.

Figure 15:
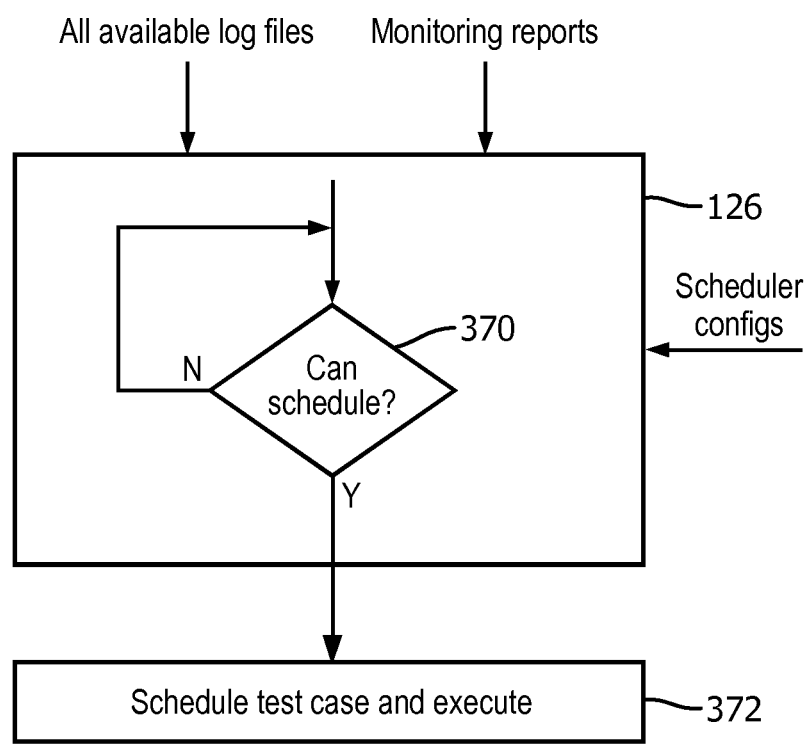
FIG. 15 shows a method for scheduling test cases for execution by one or more imaging devices such as can be performed by the dynamic model builder scheduler, in accordance with various aspects described herein.

FIG. 15 shows a method for scheduling test cases for execution by one or more imaging devices such as can be performed by the dynamic model builder scheduler 126, in accordance with various aspects described herein. After receiving all available log files and monitoring reports, at 370 a determination is made regarding a given test case can be scheduled for execution based on one or more criteria (time since last execution, imaging device availability, operational status, etc.). If the determination at 370 is negative for failing to meet one or more criteria, then the method iteratively loops in order to continue to attempt scheduling of the test case protocol. If the determination at 370 is positive, then at 372 the test case is scheduled for execution.

The proposed approach produces several test cases, which are representative of actual device usage in the field. In the case of magnetic resonance imaging (MRI), test cases are then converted into MRI exam cards to carry out device testing.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A system that facilitates generating a test script for a medical imaging device, comprising:
    a field log file database having stored thereon field log files comprising data related to examinations performed by one or more imaging devices; and
    one or more processors configured to execute:
        a mining module configured to process the field log files stored in the database and identify prominent field usage patterns;
        a prediction module configured to predict future workflow patterns by processing the field log files stored in the database; and
        a test case preparation and execution module configured to generate and execute at least one test script for an imaging device based at least in part on the identified usage patterns and the future workflow patterns.

2. The system according to claim 1, further comprising:
a mined pattern update module configured to analyze new field log files to update the identified usage patterns; and
a predicted pattern update module configured to analyze the new field log files to update the predicted workflow patterns.

3. The system according to claim 1, wherein the mining module is further configured to:
identify all examinations in terms of sequence of scans and parallel user interface operations performed during each examination.

4. The system according to claim 3, wherein the mining module is further configured to:
represent identified examinations in a tree data structure such that each scan of an examination is represented as a node in the tree and transition from one scan to the other scan is represented as an edge in the tree.

5. The system according to claim 4, wherein each node stores a count of a number of times the node is encountered while populating the tree, and wherein the start and the end of each exam are represented as start nodes and end nodes, respectively.

6. The system according to claim 5, wherein the mining module is further configured to:
store UI operations performed during a given examination on the end node for the given examination; and
after populating the tree with all the examinations in the log file database, store a value in each end node that represents a count of a specific examination present in the log file database and corresponding to the end node.

7. The system according to claim 6, wherein the mining module is further configured to:
identify a set of most commonly used examinations and suggest the set of most commonly used examinations as a prominent usage pattern; and
generate a probabilistic model of usage patterns and identify the most prominent field usage patterns.

8. The system according to claim 1, wherein the prediction model is further configured to build a long short term memory (LSTM) neural network by:
receiving an input layer;
densely connecting the input layer to a first LSTM layer;
executing a dropout function on the first LSTM layer to improve network regularity;
densely connecting a second LTSM layer to the first LSTM layer;
executing the dropout function on the second LSTM layer; and
densely connecting the second LSTM layer to a softmax output layer.

9. The system according to claim 1, wherein the prediction model is further configured to build a long short term memory (LSTM) neural network, and to train the LSTM neural network by:
dividing an input tensor X into batches of examinations of equal scan lengths;
rolling the LSTM neural network over to match batch scan length;
executing a categorical cross entropy function, which employs an output tensor y to compute a loss; and
executing an Adaptive Moment Estimation (ADAM) optimization function (86) to update network weights during each epoch.

10. A method of generating a test script for a medical imaging device, comprising:
receiving field log files comprising data related to examinations performed by one or more imaging devices;
processing the field log files and identifying prominent field usage patterns;
constructing and training a long short term memory (LSTM) neural network to identify future workflow patterns; and
generating and executing at least one test script for testing an imaging device based at least in part on the identified usage patterns and the future workflow patterns.

11. The method according to claim 10, further comprising:
analyzing new field log files and updating the identified usage patterns the predicted workflow patterns based on information contained in the new field log files.

12. The method according to claim 10, further comprising:
identifying all examinations in terms of sequence of scans and parallel user interface operations performed during each examination.

13. The method according to claim 12, further comprising:
representing identified examinations in a tree data structure such that each scan of an examination is represented as a node in the tree and transition from one scan to the other scan is represented as an edge in the tree.

14. The method according to claim 13, further comprising storing in each node a count of a number of times the node is encountered while populating the tree, and representing the start and the end of each examination as start nodes and end nodes, respectively.

15. The method according to claim 14, further comprising:
storing UI operations performed during a given examination on the end node for the given examination; and
after populating the tree with all the examinations in the log file database, storing a value in each end node that represents a count of a specific examination present in the log file database and corresponding to the end node.

16. The method according to claim 15, further comprising:
identifying a set of most commonly used examinations and suggest the set of most commonly used examinations as a prominent usage pattern; and
generating a probabilistic model of usage patterns and identify the most prominent field usage patterns.

17. The method according to claim 10, wherein constructing the long short term memory neural network comprises:
receiving an input layer;
densely connecting the input layer to a first LSTM layer;
executing a dropout function on the first LSTM layer to improve network regularity;
densely connecting a second LTSM layer to the first LSTM layer;
executing the dropout function on the second LSTM layer; and
densely connecting the second LSTM layer to a softmax output layer.

18. The method according to claim 10, wherein training the LSTM neural network comprises:
dividing an input tensor X into batches of examinations of equal scan lengths;
rolling the LSTM neural network over to match batch scan length;
executing a categorical cross entropy function, which employs an output tensor y to compute a loss; and executing an Adaptive Moment Estimation (ADAM) optimization function to update network weights during each epoch.

19. A method of predicting future workflow patterns for medical imaging devices, comprising:
    identifying all examinations E, performed by a plurality of medical imaging devices, in terms of sequence of scans;
    constructing a long short term memory (LSTM) Neural Network model for predicting future workflows;
    generating a dictionary, D, of scan names and user interface operations by collecting unique scan names over all examinations; and
    generating a one hot encoding of E by identifying an index of each dictionary word of E in D.

20. The method according to claim 19, further comprising:
    determining a probability for each of a plurality of words in the dictionary, D; and
    predicting future workflows as a function of the determined probabilities.

21. A system that facilitates generating test cases for execution in imaging devices using information from data log files from a plurality of imaging devices, comprising:
    a plurality of imaging devices that generate log files;
    a log file database that stores the log files; and
    one or more processors configured to:
        identify workflows comprising sequences of scan operations performed by the imaging devices;
        identify unintended invalid usage patterns and unintended valid usage patterns in the identified workflows;
        generate test case sequences for at least one of new scan products and scan product updates; and
        schedule the test case sequences for execution on one or more of the plurality of imaging devices in order to test at least one of the new scan products and scan product updates.

22. The system according to claim 21, wherein the one or more processors are further configured to:
    identify a frequency of occurrence of each of a plurality of sequences of sequential operations;
    generate a conditional probability tree describing the sequential operations;
    identify parallel operations corresponding to the identified sequential operations;
    for each sequential operation, generate usage distribution information for the identified parallel operations corresponding to the sequential operation; and
    generate at least one test case sequence based on the identified sequential operations, corresponding parallel operations, conditional probability tree, and usage distribution information.

23. The system according to claim 22, wherein the one or more processors are further configured to:
    generate a usage report and a performance report including a summary comprising information related to the frequency and identity of identified sequential operations, the corresponding parallel operations, the conditional probability tree, and the usage distribution information; and
    transmit the usage report and performance report to a remote server.

24. The system according to claim 22, wherein the one or more processors are further configured to:
    generate the at least one test case sequence by predicting future workflows based on the identified sequential operations, the corresponding parallel operations, and the conditional probability tree; and
    submit the at least one test case sequence for verification.

25. The system according to claim 24, wherein the usage and performance reports include information for triaging field service problems based at least in part on conditional probability distribution information.

26. The system according to claim 22, wherein the one or more processors are configured to iteratively update the at least one test case sequence based on the usage distribution information.

27. The system according to claim 26, wherein the at least one test case sequence is a scan sequence for a newly introduced scan protocol.

* * * * *